(12) United States Patent
Ohtsuka et al.

(10) Patent No.: US 7,738,107 B2
(45) Date of Patent: Jun. 15, 2010

(54) SURFACE PLASMON ENHANCED FLUORESCENCE SENSOR AND FLUORESCENCE DETECTING METHOD

(75) Inventors: Hisashi Ohtsuka, Kanagawa-ken (JP); Morihito Ikeda, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/859,027

(22) Filed: Sep. 21, 2007

(65) Prior Publication Data

US 2008/0074671 A1 Mar. 27, 2008

(30) Foreign Application Priority Data

Sep. 21, 2006 (JP) .............................. 2006-255374
Mar. 7, 2007 (JP) .............................. 2007-057098

(51) Int. Cl.
  *G01N 21/55* (2006.01)
(52) U.S. Cl. ...................................... 356/445; 356/448
(58) Field of Classification Search ......... 356/445–448; 422/82.08, 82.09, 82.11; 436/518; 250/458.1; 435/287.2
  See application file for complete search history.

(56) References Cited

U.S. PATENT DOCUMENTS

| | | | | |
|---|---|---|---|---|
| 5,064,619 A | * | 11/1991 | Finlan ...................... | 422/82.05 |
| 5,341,215 A | * | 8/1994 | Seher .......................... | 356/445 |
| 5,629,213 A | * | 5/1997 | Kornguth et al. ............ | 436/518 |
| 6,180,288 B1 | * | 1/2001 | Everhart et al. ................ | 430/2 |
| 6,330,062 B1 | * | 12/2001 | Corn et al. ................... | 356/445 |
| 6,784,999 B1 | * | 8/2004 | Tao et al. .................... | 356/445 |
| 6,807,323 B2 | * | 10/2004 | Beom et al. .................... | 385/12 |
| 6,956,651 B2 | * | 10/2005 | Lackritz et al. ............. | 356/445 |
| 6,992,770 B2 | * | 1/2006 | Naya .......................... | 356/445 |

(Continued)

FOREIGN PATENT DOCUMENTS

EP    0353937 A1    2/1990

(Continued)

OTHER PUBLICATIONS

Makio Tokunaga"Total Internal Reflection Fluorescence Microscopy that Enables Observation of Surfaces Only with High Image Quality", "This Much Can Be Learned From Bio-Imaging", pp. 104-113, Yodosha Press and a partial translation thereof.

(Continued)

*Primary Examiner*—Sang Nguyen
(74) *Attorney, Agent, or Firm*—Sughrue Mion, PLLC

(57) ABSTRACT

A fluorescence sensor is constituted by: a light source, for emitting excitation light of a predetermined wavelength; a dielectric block, formed of a material that transmits the excitation light; a metal film, formed on a surface of the dielectric block; a non flexible film of a hydrophobic material, formed on the metal film at a film thickness within a range of 10 to 100 nm; a sample holding portion, for holding a sample such that the sample contacts the non flexible film; an incident optical system, for causing the excitation light to enter the interface between the dielectric block and the metal film through the dielectric block such that conditions for total internal reflection are satisfied; and fluorescence detecting means, for detecting fluorescence emitted by a substance within the sample, which is excited by evanescent waves that leak from the interface when the excitation light enters the interface.

12 Claims, 7 Drawing Sheets

U.S. PATENT DOCUMENTS

| | | | |
|---|---|---|---|
| 7,027,163 B2 * | 4/2006 | Angeley | 356/521 |
| 7,193,711 B2 * | 3/2007 | Rassman et al. | 356/369 |
| 7,273,868 B2 * | 9/2007 | Yamada et al. | 514/249 |
| 7,297,961 B2 * | 11/2007 | Kang et al. | 250/458.1 |
| 2004/0023293 A1 | 2/2004 | Kreimer et al. | |
| 2004/0091876 A1 | 5/2004 | Yabuta et al. | |
| 2005/0158850 A1 * | 7/2005 | Kubo et al. | 435/287.2 |

FOREIGN PATENT DOCUMENTS

| | | |
|---|---|---|
| EP | 0517930 A1 | 12/1992 |
| JP | 10078390 A | 3/1998 |
| JP | 2003294610 | 10/2003 |
| WO | 0206838 | 1/2002 |

OTHER PUBLICATIONS

Fang Yu et al."Surface Plasmon Field-Enhanced Fluorescence Spectroscopy Studies of the Interaction between an Antibody and Its Surface-Coupled Antigen", Analytical Chemistry, vol. 75, No. 11, pp. 2610-2617, Jun. 1, 2003.

Thorsten Lieberman and Wolfgang Knoll"Surface-Plasmon Field-Enhanced Fluorescence Spectroscopy", Colloids and Surfaces vol. 171, pp. 115-130, 2000.

* cited by examiner

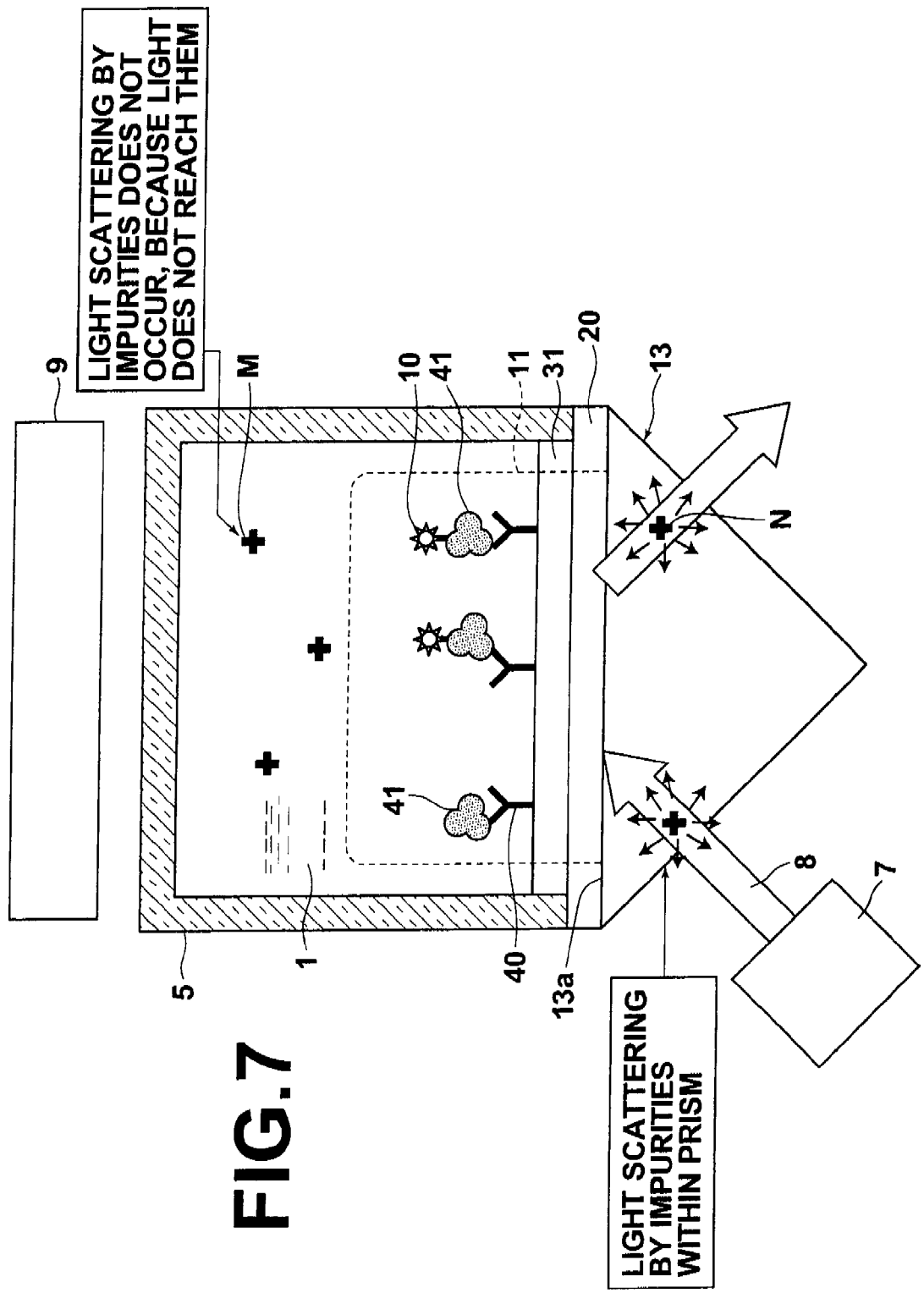

SURFACE PLASMON ENHANCED FLUORESCENCE SENSOR AND FLUORESCENCE DETECTING METHOD

BACKGROUND OF THE INVENTION

1. Field of the Invention

The present invention relates to a fluorescence sensor that detects specific substances within samples by fluorometry. More specifically, the present invention relates to a fluorescence sensor that performs surface plasmon enhancement.

2. Description of the Related Art

Fluorometry is conventionally used in for biological measurements and the like, as an easy and highly sensitive measuring method. In fluorometry, a sample, which is considered to contain a detection target substance that emits fluorescence when excited by light having a specific wavelength, is irradiated with an excitation light beam of the aforementioned specific wavelength. The presence of the detection target substance can be confirmed by detecting the fluorescence due to the excitation. In the case that the detection target substance is not a fluorescent substance, a substance labeled by a fluorescent substance that specifically bonds with the detection target substance is caused to contact the sample. Thereafter, fluorescence is detected in the same manner as described above, thereby confirming the presence of the bond, that is, the detection target substance.

FIG. 3 is a diagram that illustrates the schematic structure of an example of a sensor that performs fluorometry employing the aforementioned labeled substance. The fluorescence sensor is that which detects antigens 2 included in a sample 1. Primary antibodies 4 that specifically bond with the antigens 2 are coated on a substrate 3. The sample 1 is caused to flow through sample holding portion 5 provided above the substrate 3. Next, secondary antibodies 6, which are labeled with a fluorescent substance 10 and also bond specifically with the antigens 2, are caused to flow through the sample holding portion 5. Thereafter, a light source 7 emits an excitation light beam 8 toward the surface of the substrate 3, and a photodetector 9 detects fluorescence. At this time, if a predetermined fluorescence is detected by the photodetector 9, bonds between the secondary antibodies 6 and the antigens 2, that is, the presence of the antigens 2 within the sample 1, is confirmed.

Note that in the above example, the presence of the secondary antibodies 6 is actually confirmed by detecting the fluorescence. However, if the secondary antibodies 6 do not bond with the antigens 2, then they will flow past the substrate 3, and will not be present thereon. Therefore, the presence of the antigens 2 is indirectly confirmed, by confirming the presence of the secondary antibodies 6.

With recent advances in the performance of photodetectors, such as cooled CCD's, fluorometry has become indispensable in biological research. In addition, fluorometry has come to be widely used in fields other than biology.

However, in conventional surface plasmon enhanced fluorescence sensors such as that illustrated in FIG. 3, the excitation light beam reflected or scattered at the interface between the substrate and the sample, and light scattered by impurities other than the detection target substance becomes noise. Therefore, even if the performance of photodetectors is improved, the S/N ratio in fluorescence detection does not.

As a solution to this problem, evanescent wave fluorometry, that is, fluorometry that employs evanescent waves, has been proposed in A. Kusumi et al., "This Much Can Be Learned From Bio Imaging", pp. 104-113, Yodosha Press. An example of a fluorescence sensor that performs evanescent wave fluorometry is illustrated in FIG. 4. Note that in FIG. 4, elements which are the same as those illustrated in FIG. 3 are denoted with the same reference numerals, and detailed descriptions thereof will be omitted unless particularly necessary (the same applies to all of the following descriptions).

In this fluorescence sensor, a prism 13 (dielectric block) is employed instead of the substrate 3. The excitation light beam 8 emitted from the light source 7 is irradiated through the prism 13 such that conditions for total internal reflection at the interface between the prism 13 and the sample 1 are satisfied. In this configuration, the secondary antibodies 6 are excited by evanescent waves 11 that leak in the vicinity of the interface when the excitation light beam 8 is totally internally reflected thereat. Fluorescence detection is performed by the photodetector 9, which is provided at the side opposite the prism 13 from the sample 1 (the upper portion in FIG. 4).

In this fluorescence sensor the excitation light beam 8 is totally internally reflected toward the lower portion of the drawing, and fluorescence detection is performed from above. Therefore, detected excitation light components do not become a background for a fluorescence detection signal. In addition, the evanescent waves 11 only reach a region of several hundred nm from the interface. Therefore, scattering due to impurities M within the sample 1 can be virtually eliminated. For these reasons, evanescent fluorometry is being noticed as a method that enables fluorescent measurement of detection target substances in units of single molecules, while greatly reducing (light) noise compared to conventional fluorometry.

A surface plasmon enhanced fluorescence sensor, such as that illustrated in FIG. 5, is also known as a sensor capable of fluorescence measurement at even higher sensitivity. The surface plasmon enhanced fluorescence sensor is disclosed, for example, in Japanese Patent No. 3562912, and differs from the fluorescence sensor of FIG. 4 in that a metal film 20 is formed on the prism 13. That is, surface plasmon is generated within the metal film 20 when the excitation light beam 8 is irradiated thereon, and the electric field amplification effect provided thereby enhances the fluorescence. According to a simulation, the fluorescent intensity has been shown to be enhanced 1000 times.

However, in the aforementioned surface plasmon enhanced fluorescence sensor, if the fluorescent substance within the sample and the metal film are too close to each other, the energy excited within the fluorescent substance is transferred to the metal film before fluorescence is emitted. That is, a phenomenon in which fluorescence does not occur (so called metallic light loss) may occur.

Fang Yu et al. propose forming a SAM (Self Assembled Membrane) on the metal film, to separate the fluorescent substance within the sample from the metal film at least by a distance equal to the thickness of the SAM, in "Surface Plasmon Field-Enhanced Fluorescence Spectroscopy Studies of the Interaction between an Antibody and Its Surface-Coupled Antigen", Analytical Chemistry, Vol. 75, pp. 2610-2617, 2003. Note that FIG. 5 illustrates the SAM, denoted by reference number 21. T. Liebermann et al. also discuss the dependency of the fluorescence intensity enhanced by surface plasmon on the distance from the metal film, related to metallic light loss, in "Surface-Plasmon Field-enhanced fluorescence Spectroscopy", Colloids and Surfaces 171, pp. 115-130, 2000.

However, when fluorescence detection was performed using the aforementioned surface plasmon enhanced fluorescence sensor provided with the SAM, it was found that the sensitivity of fluorescence detection was not improved much, compared to a case in which the SAM is not provided.

SUMMARY OF THE INVENTION

The present invention has been developed in view of the foregoing circumstances. It is an object of the present invention to provide a surface plasmon enhanced fluorescence sensor, which is capable of detecting fluorescence with extremely high sensitivity.

It is another object of the present invention to provide a fluorescence detecting method using a surface plasmon enhanced fluorescence sensor as described above, which is capable of detecting fluorescence with extremely high sensitivity.

A surface plasmon enhanced fluorescence sensor of the present invention provides a non flexible film instead of the SAM to achieve the desired objective. More specifically, the surface plasmon enhanced fluorescence sensor of the present invention comprises:

a light source, for emitting an excitation light beam of a predetermined wavelength;

a dielectric block, formed of a material that transmits the excitation light beam;

a metal film, formed on a surface of the dielectric block;

a non flexible film of a hydrophobic material, formed on the metal film at a film thickness within a range of 10 to 100 nm;

a sample holding portion, for holding a sample such that the sample contacts the non flexible film;

an incident optical system, for causing the excitation light beam to enter the interface between the dielectric block and the metal film through the dielectric block such that conditions for total internal reflection are satisfied; and fluorescence detecting means, for detecting fluorescence emitted by a substance within the sample, which is excited by evanescent waves that leak from the interface when the excitation light beam enters the interface.

A film formed by a polymer may be employed as the non flexible film. In the case that the non flexible polymer film is employed, it is desirable for hydrophilic linkers, for bonding with a specific substance, to be formed on the non flexible polymer film.

In the surface plasmon enhanced fluorescence sensor of the present invention, it is desirable for capture molecules, for bonding with a specific substance, to be immobilized on the non flexible film. It is desirable for the capture molecules to be those that bond with second messengers within living tissue. A second messenger is a substance that cause intracellular signals to be transmitted, by sensing a bond between a receptor and a ligand (agonist), when stimulus from outside a cell is communicated to the interior of the cell via an intracellular communications system by the bond between the receptor and the ligand. Examples of second messengers include cAMP and inositol phosphate. Preferably, the second messengers are cAMP.

It is preferable for the surface plasmon enhanced fluorescence sensor of the present invention to further comprise: a kit that causes a labeled substance, which is an integrated substance constituted by the substance that directly bonds with the capture molecules and a fluorescent substance excited by the evanescent waves, to be included within the sample.

Meanwhile, the fluorescence detecting method of the present invention is a method that employs the aforementioned surface plasmon enhanced fluorescence sensor, having the capture molecules that bond with a specific substance immobilized on the non flexible film, comprising the steps of:

causing a labeled substance, which is an integrated substance constituted by the substance that directly bonds with the capture molecules (such as the aforementioned second messengers) and a fluorescent substance excited by the evanescent waves, to be included within the sample; and detecting the fluorescence.

According to research performed by the present inventor, the reason why the sensitivity of fluorescence detection in the conventional surface plasmon enhanced fluorescence sensor provided with the SAM is not improved much is because the SAM is "spongy". Therefore, the thickness of the SAM varies easily, which causes fluorescent substances within sample liquids to approach the metal film to distances where metallic light loss occurs.

Another reason why the sensitivity of fluorescence detection in the conventional surface plasmon enhanced fluorescence sensor provided with the SAM is not improved much is because of the permeable nature of the "spongy" SAM. Therefore, molecules that cause metallic light loss, such as metal ions and dissolved oxygen which are present in sample liquids, enter the interior of the SAM. These molecules rob the excitation energy of excitation light beams.

The surface plasmon enhanced fluorescence sensor of the present invention provides the non flexible film having a thickness of 10 to 100 nm on the metal film, based on the above discoveries. Therefore, fluorescent substances within sample liquids can be prevented from approaching the metal film to distances where metallic light loss occurs. According to this sensor, the aforementioned metallic light loss cannot occur, the electric field amplification effect of surface plasmon can be positively obtained, and fluorescence can be detected at extremely high sensitivity.

In addition, in the surface plasmon enhanced fluorescence sensor of the present invention, the non flexible film is formed by hydrophobic material, based on the above discoveries. Therefore, molecules that cause light loss, such as metal ions and dissolved oxygen, which are present within sample liquids, are prevented from entering the interior of the non flexible film. Accordingly, the excitation energy of excitation light beams can be prevented from being robbed by these molecules. Therefore, the surface plasmon enhanced sensor of the present invention can secure extremely high excitation energy, and fluorescence can be detected at extremely high sensitivity.

Note that "non flexible" means that the film has rigidity to a degree that it will not deform such that the thickness thereof changes during normal use of the sensor.

The lower and upper limits of the film thickness are set to 10 nm and 100 nm for the following reasons. Light loss occurs in molecules of fluorescent substances which are present in the vicinity of metal, due to energy transition to the metal. The degree of energy transition is inversely proportionate to the distance between the molecules and the metal to the third power in the case that the metal is a plane which is infinitely thick. The degree of energy transition is inversely proportionate to the distance between the molecules and the metal to the fourth power in the case that the metal is a plane which is infinitely thin. The degree of energy transition is inversely proportionate to the distance between the molecules and the metal to the sixth power in the case that the metal is in the form of fine particles. As taught in the aforementioned document by T. Liebermann, it is desirable for a distance of several nm or greater, preferably 10 nm or greater, to be secured between the metal and the fluorescent substance molecules in the case that the metal is a metal film. Accordingly, the lower limit of the film thickness is set to 10 nm in the present invention.

On the other hand, the fluorescent substance molecules are excited by the evanescent waves which leak from the surface of the metal film and which are amplified by surface plasmon.

The range of travel (distance from the surface of the metal film) of evanescent waves is at most approximately one wavelength, and it is known that the electric field intensity thereof attenuates drastically at an exponential rate corresponding to the distance from the surface of the metal film. FIG. 6 illustrates calculation results of the relationship between the electric field intensity and the distance from the metal film, for visible light having a wavelength of 635 nm. As can be seen from the graph of FIG. 6, leakage of the evanescent wave occurs only for a distance approximately corresponding to the wavelength (635 nm), and the electric field intensity drops drastically beyond 100 nm. It is desirable for the electric field that excites the fluorescent substance molecules to be as great as possible. Therefore, it is desirable to set the distance between the surface of the metal film and the fluorescent substance molecules to be 100 nm or less, to perform effective excitation. Accordingly, the upper limit of the film thickness is set to 100 nm in the present invention.

Here, an example of a preferable material that possesses the aforementioned desired properties is a polymer. However, in many cases, proteins and the like which are present within sample liquids are easily nonspecifically adsorbed on to polymers. In the case that antigens which are specifically adsorbed onto antibodies which are coated on the surface of the non flexible film are to be detected by fluorometry, for example, the non specific adsorption of the proteins yields the same result as the specific adsorption of the antigens, which may cause false positive detection to occur.

Therefore, in the case that a non flexible polymer film is employed, if hydrophilic linkers are formed on then on flexible film, the linkers block the proteins and the like. Therefore, the proteins and the like are prevented from being non specifically adsorbed on to the non flexible film, and false positive detection is prevented. Meanwhile, antibodies and the like which are to be provided on the surface of the non flexible film may be specifically bonded with the linkers, to be supplied on the surface of the non flexible film.

More specific examples of materials of the non flexible film are hydrophobic high polymers and films that contain inorganic oxides.

Hydrophobic polymers to be utilized in the present invention preferably include monomers, which have solubilities of 20% by weight with respect to water, at 50% by weight or greater.

The solubility of a monomer that forms a hydrophobic polymer with respect to water at a temperature of 25° C. can be measured by the method described in "New Basic Techniques for Experimental Chemistry" (Maruzen Chemical, 1975). The solubilities of monomers to be utilized in the present invention with respect to water at a temperature of 20° C. measured by this method are: 0.00% by weight for 2 ethyl hexyl methacrylate; 0.03% by weight for styrene; 1.35% by weight for methyl methacrylate; 0.32% by weight for butyl acrylate; and 0.03% by weight for butyl methacrylate. As an index for solubility of the hydrophobic high polymer film to be used in the present invention with respect to water is preferably 10% by weight or less, and further 1% by weight or less.

Specific examples of the monomers having solubilities of 20% by weight or less with respect to water to be used in the present invention include: vinyl esters; acrylates; methacrylates; olefins; styrenes; crotonates; itaconic acid esters; maleate esters; fumarate esters; allyl compounds; vinyl ethers; and vinyl ketones. Styrene, methacrylate methyl, methacrylate hexafluoropropane, vinyl acetate, and acrylonitryl may be used. A homopolymer constituted by a single type of monomer, or a copolymer constituted by two or more types of monomers may be used as the hydrophobic high polymer compound.

In the present invention, a high polymer compound, which is a copolymer of a monomer that has a solubility of 20% by weight or less with respect to water and a monomer that has a solubility of 20% by weight or greater, may be employed. Specific examples of monomers that have solubilities of 20% by weight or greater with respect to water include: methacrylate 2-hydroxy ethyl; methacrylate; acrylate; and allyl alcohol.

Polyacrylates, polymethacrylates, polyester, and polystyrene are preferable as the hydrophobic high polymers to be employed in the present invention. By employing these hydrophobic high polymers, film formation is facilitated, and at the same time, exposure of functional bases for immobilizing biologically active substances thereon is also facilitated. For example, it is easy to expose carboxyl bases and hydroxyl bases on a film formed by polyacrylate, polymethacrylate, or polyester, by performing hydrolysis of the surface with an acid or a base. It is easy to expose carboxyl bases on a film formed by polystyrene, by administering oxidation treatment, such as a UV/ozone treatment, on the surface.

Silica, alumina, titania, zirconia, ferrite, composites, and derivatives thereof may be utilized as the inorganic oxides in the present invention. Conventional methods may be used to form the film. Examples of methods which may be used to form the film include: the sol gel method; the sputtering method; the vapor deposition method; and the plating method.

In the case that the capture molecules that bond with a specific substance, such as second messengers within living tissue, are provided on the non flexible film of the surface plasmon enhanced fluorescence sensor of the present invention, so called "competitive" fluorescence detection can be favorably adopted. If the competitive fluorescence detection is adopted, because fluorescence detection with high sensitivity is enabled by the surface plasmon enhancement, B/F separation (Bound/Free separation), which had heretofore been considered difficult with "sandwich" fluorescence detection using two types of capture molecules, can be obviated, while high sensitivity can be realized at the same time. If B/F separation can be obviated, deterioration in sensitivity that occurs due to cleansing fluctuations in the competitive detecting method can be prevented.

Note that the capture molecules are not limited to any particular molecule, as long as they are molecules that bond with a specific substance. Examples of the capture molecules include: antibodies; fragments of antibodies; adaptors constituted by nucleic acid; inclusion compounds; and template molecules constructed by molecular imprinting. Dissociation equilibrium constants (Kd) are indices that represent the bonding properties of capture molecules with respect to specific substances. In the present invention, capture molecules having dissociation equilibrium constants Kd of $10^{-6}$ or less, more preferably $10^{-7}$ or less, and even more preferably $10^{-8}$ or less are selected. It is desirable for capture molecules that have bonding properties with respect to a specific substance, but do not have bonding properties with respect to other substances, that is, capture molecules having specificity, to be selected and utilized.

Particularly in the case that the capture molecules are those that bond with second messengers within living tissue, the activation of receptors by ligands or inhibition of receptors can be detected or quantized, by measuring the amount of second messengers. In this case as well, the surface plasmon enhancement enables detection and/or quantization of the second messengers with high sensitivity.

The surface plasmon enhanced fluorescence sensor may be equipped with a kit that causes a labeled substance, which is an integrated substance constituted by the substance (such as the second messengers) that directly bonds with the capture molecules and a fluorescent substance excited by the evanescent waves, to be included within the sample. In this case, the kit can be used to easily introduce a labeled specific substance into the sample. Therefore, the aforementioned competitive fluorescence detection can be performed extremely easily.

Note that the labeled specific substance may be introduced to the sample in advance. Alternatively, the labeled specific substance may be introduced to the sample after a predetermined amount of time elapses after the sample contacts the capture molecules. As a further alternative, the labeled specific substance may be caused to contact the capture molecules, and after a predetermined amount of time elapses, the sample may be mixed therein.

BRIEF DESCRIPTION OF THE DRAWINGS

FIG. 7 is a side view that illustrates the schematic structure of a surface plasmon enhanced fluorescence sensor according to a third embodiment of the present invention.

BEST MODE FOR CARRYING OUT THE INVENTION

Embodiments of the present invention will be described hereinafter, with reference to the attached drawings.

Figure 1:
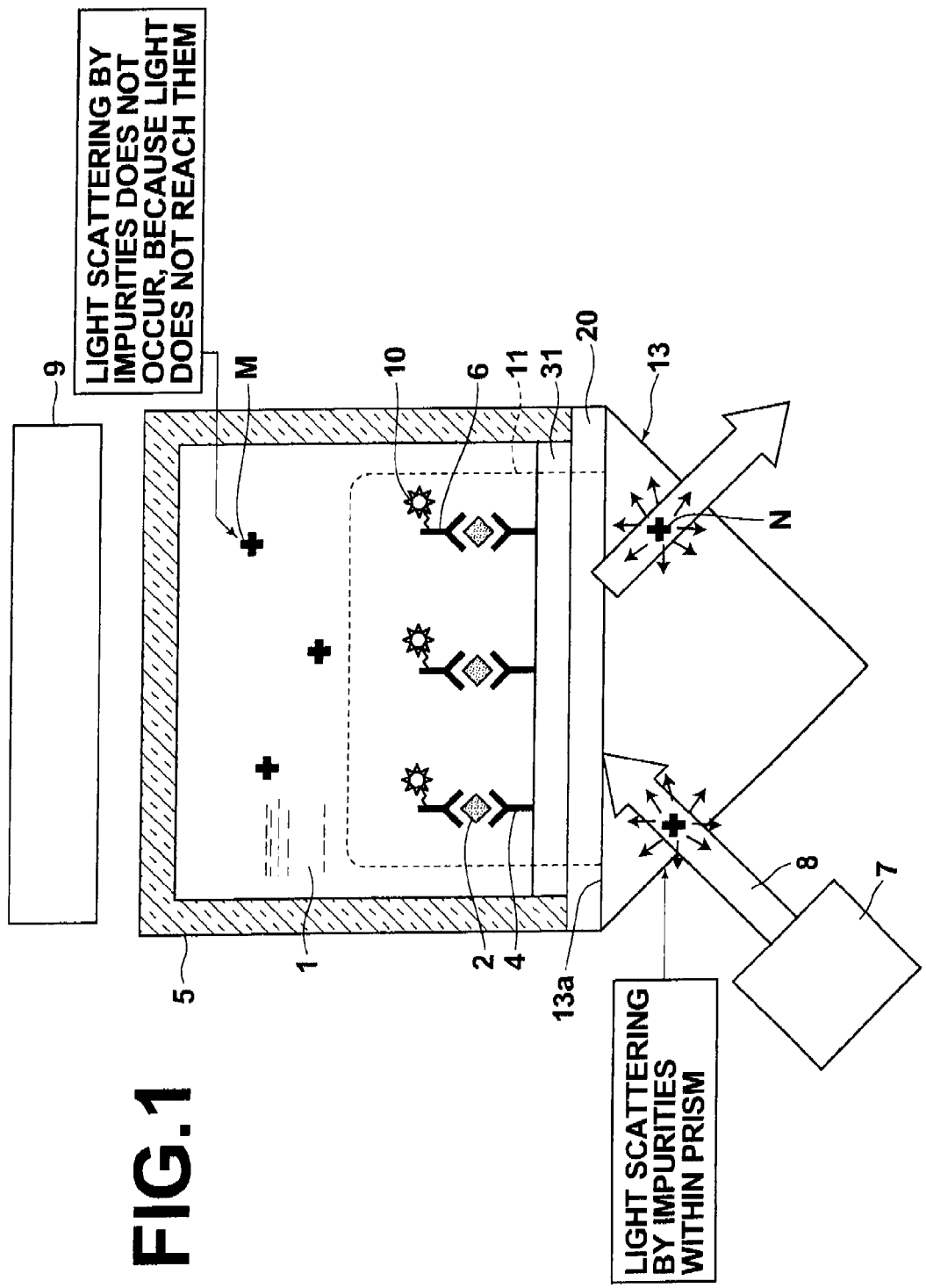
FIG. 1 is a side view that illustrates the schematic structure of a surface plasmon enhanced fluorescence sensor according to a first embodiment of the present invention.

FIG. 1 is a side view that illustrates the schematic structure of a surface plasmon enhanced fluorescence sensor (hereinafter, simply referred to as "fluorescence sensor") according to a first embodiment of the present invention. As illustrated in FIG. 1, the fluorescence sensor comprises: a semiconductor laser light source 7, for emitting an excitation light beam 8 having a wavelength of 635 nm, for example; a prism 13 (dielectric block), formed of a material that transmits the excitation light beam 8 and provided at a position such that the excitation light beam 8 enters it at an end facet thereof; a metal film 20, formed on a surface 13a of the dielectric block 13; a non flexible polymer film, formed on the metal film 20; a sample holding portion 5, for holding a liquid sample 1 such that the liquid sample 1 contacts the non flexible polymer film 31 at the side opposite the prism 13; and photodetector 9 (fluorescence detecting means), provided above the sample holding portion 5.

Note that in the present embodiment, the light source 7 is provided such that the excitation light beam 8 enters the interface between the dielectric block 13 and the metal film 20 through the dielectric block 13 such that conditions for total internal reflection are satisfied. That is, the light source 7 itself functions as an incident optical system that causes the excitation light beam 8 to enter the prism 13 in the manner described above. However, the present invention is not limited to this construction, and an incident optical system constituted by lenses, mirrors, and the like, that causes the excitation light beam 8 to enter the prism 13 in the above manner may be provided separately.

The prism 13 may be formed by ZEONEX™ 330R (refractive index: 1.50) by Japan Zeon K. K. Meanwhile, the metal film 20 is formed by sputtering gold onto the surface 13a of the prism 13, at t film thickness of 50 nm. The non flexible film 31 is formed by spin coating a polystyrene polymer having a refractive index of 1.59 onto the metal film 20, at a film thickness of 20 nm.

Note that the prism 13 may be formed by materials other than that described above, such as known resins and optical glass. It can be said that resins are preferable over optical glass, from the viewpoint of cost. In the case that the prism 13 is to be formed by resin, polymethyl methacrylate (PMMA), polycarbonate (PC), and non crystalline polyolefin (APO) that includes cycloolefin may be favorably employed.

LAS-1000 by FUJIFILM Corp. may be employed as the photodetector 9.

The detection targets of the fluorescence sensor are CRP antigens 2 (molecular weight: 110000 Da), for example. Primary antibodies 4 (monoclonal antibodies) that specifically bond with the CRP antigens 2 are immobilized on the non flexible film 31. The primary antibodies 4 are immobilized on the non flexible polymer film 31 via PEG's, of which the ends are carboxylized, by the amine coupling method. Meanwhile, monoclonal antibodies having different epitopes from the primary antibodies 4 are employed as the secondary antibodies 6. The secondary antibodies 6 are labeled with a fluorescent substance 10 (Cy5 pigment).

The amine coupling method comprises the following steps, for example. Note that the following example is for a case that a 30 µl (micro liter) cuvette/cell is employed.

1) Activate —COOH Bases at the Tips (Ends) of Linkers

30 µl of a solution, which is an equal volume mixture of 0.1M NHS and 0.4M EDC, is added, and left at room temperature for 30 minutes.
NHS: N-hydrooxysuccinimide
EDC: 1-ethyl-3-(3-dimethylaminopropyl) carbodiimide 2) Immobilize Primary Antibodies 4

Perform five cleansing operations with a PBS buffer (pH: 7.4), add 30 µl of a primary antibody solution (500 µg/ml), and leave at room temperature for 30 to 60 minutes.

3) Block Non Reactive —COOH Bases

Perform five cleansing operations with a PBS buffer (pH: 7.4), add 30 µl of 1M ethanol amine (pH: 8.5), then leave at room temperature for 20 minutes. Thereafter, perform five more cleansing operations with a PBS buffer (pH: 7.4).

Meanwhile, the light source 7 is not limited to the semiconductor laser, and other known light sources may be selected and utilized. The photodetector 9 is also not limited to that described above, and other known photodetectors, such as CCD's, PD's (photodiodes), photomultiplier tubes, and c-MOS's may be employed. In addition, if the excitation wavelength is changed, pigment other than Cy5 maybe used as the labeled substance.

Hereinafter, the operation of the fluorescence sensor will be described for a case in which CRP antigens 2 included in the liquid sample 1 are to be detected. Note that the method that will be described here is a so called "sandwich" detection method, wherein the CRP antigens 2 are detected when they are sandwiched between two types of antibodies. First, the liquid sample 1 is caused to flow through the sample holding portion 5. Next, the secondary antibodies 6, which are labeled with the fluorescent substance 10 and specifically bond with the CRP antigens 2, are caused to flow through the sample holding portion 5. Note that the Cy5 pigment emits fluorescence of a predetermined wavelength when excited by excitation light having a wavelength of 635 nm.

Thereafter, the excitation light beam 8 is emitted from the light source 7 toward the prism 13, and fluorescence detection is performed by the photodetector 9. At this time, evanescent waves 11 leak from the interface between the prism 13 and the metal film 20. If the CRP antigens 2 are bonded to the primary antibodies 4 at this time, the secondary antibodies 6 are bonded to the antigens 2, and the fluorescent substance 10, which the secondary antibodies 6 are labeled with, are excited by the evanescent waves 11. The excited fluorescent substance 10 emits fluorescence of a predetermined wavelength, and the fluorescence is detected by the photodetector 9. In the case that the photodetector 9 detects the fluorescence of the predetermined wavelength, it can be confirmed that the secondary antibodies 6 are bonded to the CRP antigens 2, that is, that the CRP antigens 2 are contained in the sample 1.

Note that the evanescent waves 11 only propagate a distance of several hundreds of nanometers from the interface between the prism 13 and the metal film 20. Therefore, scattering due to impurities in the sample can be substantially eliminated. In addition, light scattered by impurities N within the prism 13 is blocked by the metal film 20, and does not reach the photodetector 9. Accordingly, the fluorescence sensor is capable of virtually eliminating light noise, and fluorescence detection having an extremely high S/N ratio is enabled.

In addition, because the fluorescence sensor of the present embodiment is provided with the metal film on the surface 13a of the prism 13, surface plasmon is excited therein. The electric field amplification effect provided by the surface plasmon enhances the fluorescence, and the S/N ratio is improved further.

In the fluorescence sensor of the present embodiment, the non flexible film 31 having a film thickness of 20 nm is formed on the metal film 20. Therefore, the fluorescent substance 10 within the sample 1 is prevented from approaching the metal film 20 to a degree that metallic light loss occurs. Accordingly, the aforementioned metallic light loss does not occur in the fluorescence sensor, the electric field amplification effect of the surface plasmon is positively obtained, and fluorescence detection with extremely high sensitivity is enabled.

The non flexible film 31 is formed by a polystyrene polymer, which is hydrophobic. Therefore, molecules that cause light loss, such as metal ions and dissolved oxygen, which are present within the sample 1, are prevented from entering the interior of the non flexible film 31. Accordingly, the excitation energy of the excitation light beam 8 can be prevented from being robbed by these molecules. Therefore, the surface plasmon enhanced sensor can secure extremely high excitation energy, and fluorescence can be detected at extremely high sensitivity.

Note that the secondary antibodies 6, which are not bonded to the CRP antigens and are at positions remote from the surface of the non flexible film 31, do not emit fluorescence, because the evanescent waves 11 do not reach them. Therefore, no problems are caused in measurement, even if such secondary antibodies 6 are present within the sample 1. Accordingly, cleansing operations, that is, B/F separation (Bound/Free separation) need not be performed after each measurement.

Figure 2:
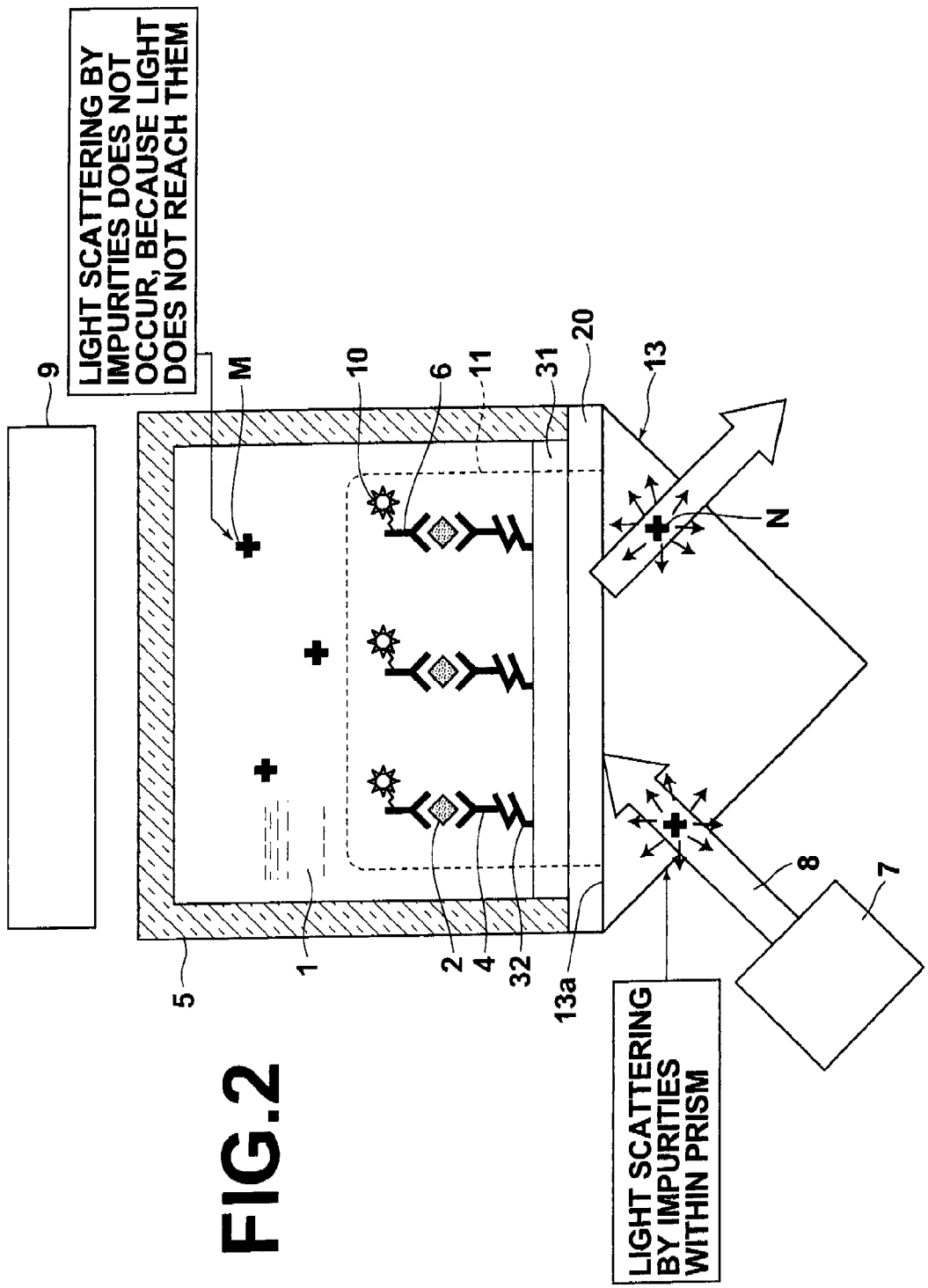
FIG. 2 is a side view that illustrates the schematic structure of a surface plasmon enhanced fluorescence sensor according to a second embodiment of the present invention.

Next, a fluorescence sensor according to a second embodiment of the present invention will be described with reference to FIG. 2. The fluorescence sensor of the second embodiment basically differs from that of the first embodiment in that hydrophilic linkers 32 are bonded to the surface of the non flexible film 31.

It is easy for the secondary antibodies 6 and the antigens 2 to be non specifically adsorbed to the surface of the non flexible film 31 formed by a polystyrene polymer. In this case, the non specific adsorption of the antibodies 6 and the antigens 2 yields the same result as the specific adsorption of the antigens 2, which may cause false positive detection of the antigens 2 to occur.

However, in the fluorescence sensor of the second embodiment, the linkers 32 that bond with the primary antibodies 4 are formed on the non flexible film 32. The linkers 32 block the secondary antibodies 6 and the antigens 2. Therefore, the secondary antibodies 6 and the antigens 2 are prevented from being non specifically adsorbed onto the non flexible film 31, and false positive detection is prevented. Meanwhile, the primary antibodies 4 which are to be provided on the surface of the non flexible film 31 may be specifically bonded with the linkers 32, to be supplied on the surface of the non flexible film 31.

Figure 3:
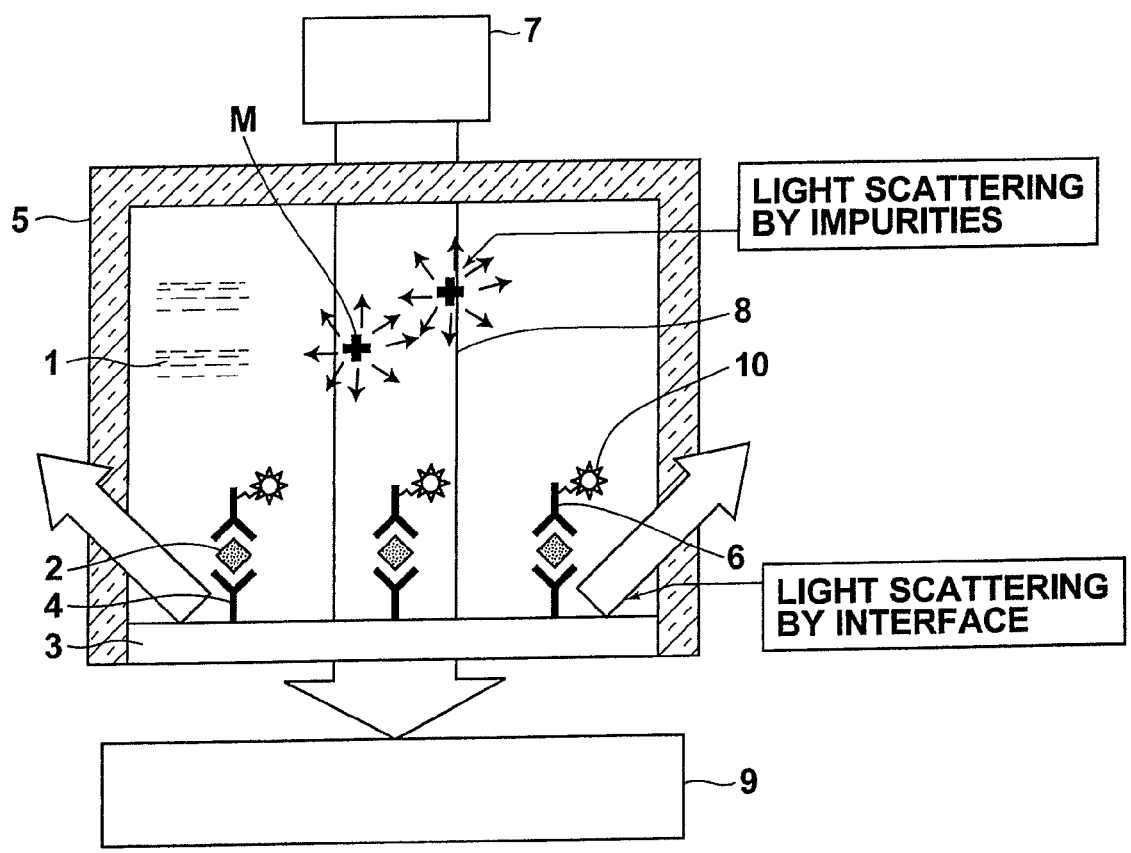
FIG. 3 is a side view that illustrates the schematic structure of a conventional fluorescence sensor.
Figure 4:
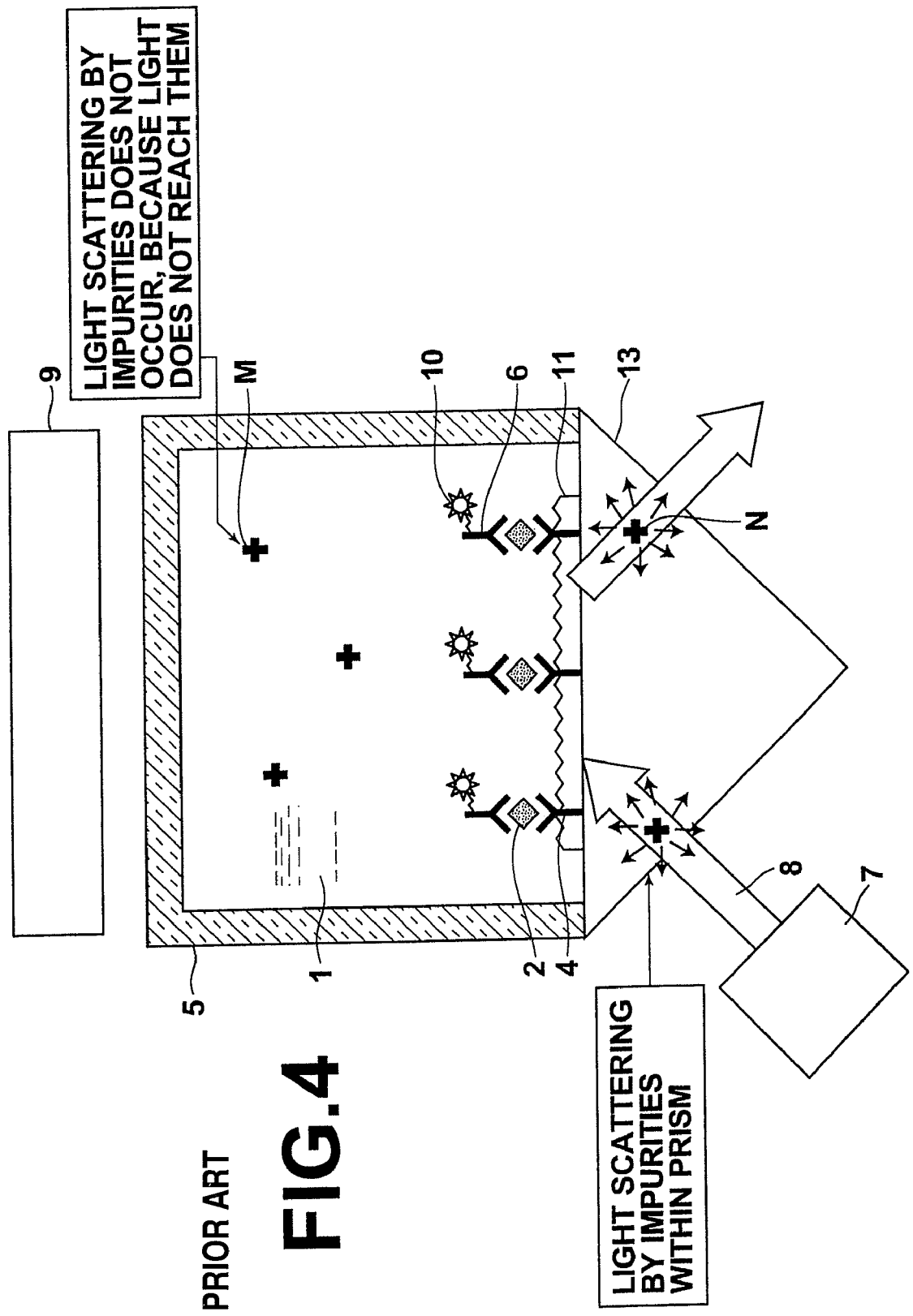
FIG. 4 is a side view that illustrates the schematic structure of another conventional fluorescence sensor.
Figure 5:
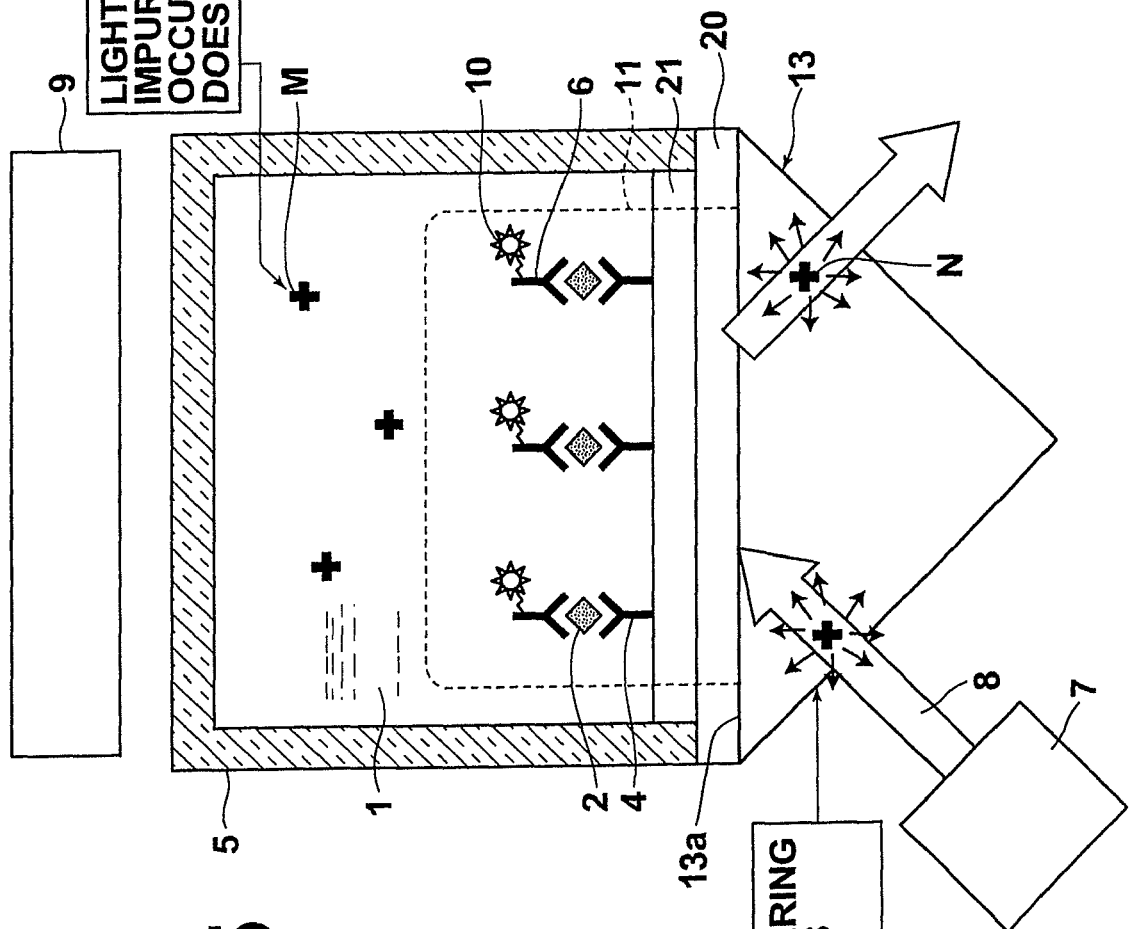
FIG. 5 is a side view that illustrates the schematic structure of still another conventional fluorescence sensor.
Figure 6:
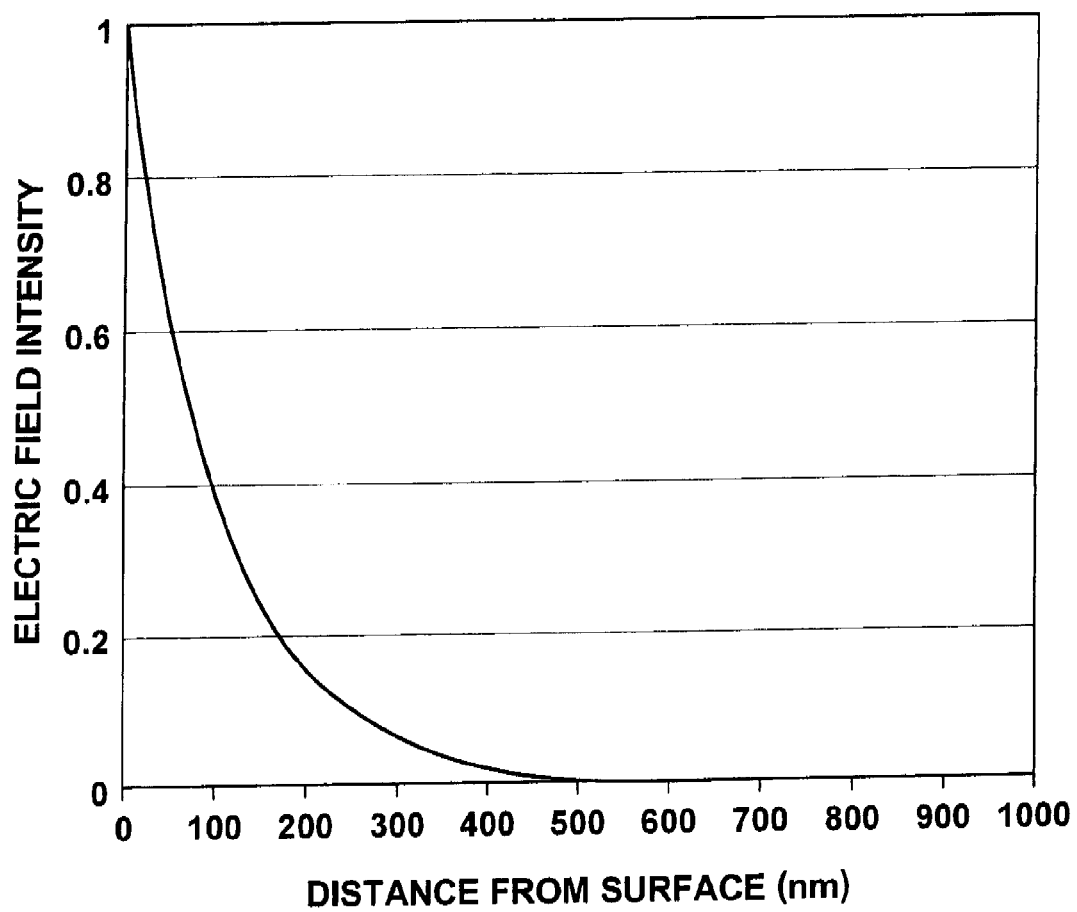
FIG. 6 is a graph that illustrates the relationship between the electric field intensity of evanescent waves and distance from the surface of a metal film.

Table 1 below compare and illustrate the detection limits of the fluorescence sensor of the second embodiment and conventional fluorescence sensors. In Table 1, the columns indicated by A, B, C, and D represent the detection limit of a conventional sensor having a basic structure as illustrated in FIG. 3, a conventional sensor that employs the ELISA method, a conventional sensor having a basic structure as illustrated in FIG. 4, and the fluorescence sensor of the second embodiment, respectively. Note that the ELISA method is a known method that amplifies fluorescence detection signals, by increasing the amount of a fluorescent substance (pigment) utilizing oxygen reactions.

The CRP antigens 2 were detected at concentrations of 50 pM (pico mol), 5 pM, 500 fM (femto mol), 50 fM, 5 fM, 500 aM (atto mol), and 50 aM. The detection limits are represented by the smallest mol concentration that each sensor was capable of detecting. As can be seen from the table, the surface plasmon enhanced fluorescence sensor of the present invention is capable of fluorescence detection at sensitivities 2 to 4 powers of 10 greater than conventional sensors.

TABLE 1

| | WITH CLEANSING (R/F SEPARATION) CONVENTIONAL FLUOROMETRY (LASER + LAS) | | REACTION 2 HOURS, WITH CLEANSING (R/F SEPARATION) ELISA METHOD | | | WITHOUT CLEANSING (B/N SEPARATION) REACTION 1 HOUR, 120 SECOND MEASUREMENT EVANESCENT FLUOROMETRY | | WITHOUT CLEANSING (B/N SEPARATION) REACTION 1 HOUR, 5 SECOND MEASUREMENT PLASMON ENHANCED FLUOROMETRY | |
|---|---|---|---|---|---|---|---|---|---|
| | | | | | CHEMICAL | | | | |
| | FIRST TIME | SECOND TIME | COLOR-ATION | FLUORESCENCE | LIGHT EMISSION | FIRST TIME | SECOND TIME | FIRST TIME | SECOND TIME |
| 50 pM | o | o | o | o | o | o | o | o | o |
| 5 pM  | x | x | o | o | o | o | o | o | o |
| 500 fM | x | x | o 640 fM | o 440 fM | o 280 fM | o 450 fM | o 450 fM | o | o |
| 50 fM | x | x | x | x | x | x | x | o | o 45 fM |
| 5 fM  | x | x | x | x | x | x | x | o 4.5 fM | x |
| 500 aM | x | x | x | x | x | x | x | — | x |
| 50 aM  | x | x | x | x | x | x | x | — | x |
| | A | | B | | | C | | D | |

Meanwhile, to improve stability with respect to environmental changes, and particularly temperature, it is preferable for the non flexible film 31 and the prism 13 to have similar coefficients of thermal expansion. That is, if the coefficients of thermal expansion of the two components are different to a great degree, separation or decrease in the degree of close contact becomes likely when temperature changes occur. Specifically, it is desirable for the difference between the coefficients of linear (thermal) expansion of the two components to be within a range of $35 \times 10^{-6}$. Note that the metal film 20 is provided between the non flexible film 31 and the prism 13. However, if temperature changes occur, the metal film 20 expands and contracts along with the non flexible film 31 above and the prism 13 below. Therefore, the fact remains that it is preferable for the coefficients of thermal expansion of the non flexible film 31 and the prism 13 to be similar. In consideration of the above points, in the case that the non flexible film 31 is formed by a polymer, it is preferable to select resin as the material of the prism 13 over glass.

Table 2 below illustrates the main substances which are employed as materials of the prism 13 and the non flexible film 31 and their coefficients of linear (thermal) expansion, along with the coefficients of linear (thermal) expansion of water and gold, as references. It is desirable for materials having coefficients of linear (thermal) expansion with differences therebetween being within the range of $35 \times 10^{-6}$ to be selected as the materials of the prism 13 and the non flexible film 31.

TABLE 2

| Material | Coefficient of Linear (Thermal) Expansion ($\times 10^{-6}$) |
|---|---|
| Water | 70 |
| Polystyrene | 70 |
| PMMA | 70 |
| Polycarbonate | 60 |
| Cycloolefin (Zeonex ™ 330R) | 90 |
| Cycloolefin (Zeonex ™ E48R) | 60 |
| Quartz (SiO$_2$) | 0.6 |
| BK7 | 7.1 |
| Gold | 14 |

Next, a fluorescence sensor according to a third embodiment of the present invention will be described with reference to FIG. 7. The fluorescence sensor of the third embodiment basically differs from that of the first embodiment in that a labeled specific substance, which is an integrated substance constituted by a substance that directly bonds with capture molecules, such as antibodies, and a fluorescent substance excited by the evanescent waves, are included within the sample.

When detection and/or quantization of a substance contained in the sample 1 is performed using the fluorescence sensor of the third embodiment, so called competitive fluorescence detection is performed. Hereinafter, the competitive fluorescence detection will be described. In the present embodiment, second messengers 41, which are present within living tissue, are the detection targets, and capture molecules 40 that directly bond with the second messengers 41 are employed.

The labeled specific substance, which is an integrated substance constituted by the fluorescent substance 10 and the second messengers 41, is also contained in the sample 1. Note that the labeled specific substance may be contained in the sample 1 in advance. Alternatively, the labeled specific substance may be introduced to the sample 1 after a predetermined amount of time elapses after the sample 1 contacts the capture molecules 40. As a further alternative, the labeled specific substance may be caused to contact the capture molecules 40, and after a predetermined amount of time elapses, the sample 1 may be mixed therein. The labeled specific substance may be sold with the fluorescence sensor, or as a kit to be employed with the fluorescence sensor. In these cases, the labeled specific substance is readily available to users of the sensors, which is favorable because competitive fluorescence detection can be easily executed.

In the competitive fluorescence detection, the greater the number of second messengers 41, which are the targets of detection, within the sample 1, the less the amount of the labeled specific substance (and in turn, the fluorescent substance 10) that bonds with the capture molecules 40. Accordingly, the lower the intensity of detected surface plasmon enhanced fluorescence, the greater the number of second messengers 41 within the sample. Detection and/or quantization of the second messengers 41 can be performed based on this principle.

In this case as well, the aforementioned surface plasmon enhancement effect can be obtained. Therefore, the second messengers 41 can be detected with high sensitivity, and detection and/or quantization of low molecular compounds, which is difficult with the sandwich detection method, can be easily executed.

What is claimed is:

1. A surface plasmon enhanced fluorescence sensor, comprising:
    a light source that emits an excitation light beam of a predetermined wavelength;
    a dielectric block formed of a material that transmits the excitation light beam;
    a metal film formed on a surface of the dielectric block;
    a non flexible film of a hydrophobic material formed on the metal film at a film thickness within a range of 10 to 100 nm;
    a sample holding portion that holds a sample such that the sample contacts the non flexible film;
    an incident optical system that causes the excitation light beam to enter an interface between the dielectric block and the metal film through the dielectric block such that conditions for total internal reflection are satisfied; and
    fluorescence detecting means, for directly detecting fluorescence emitted by a substance within the sample, which is excited by evanescent waves that leak from the interface when the excitation light beam enters the interface,
    wherein the fluorescence detecting means is provided on a side of the interface in contact with the sample and provided above the sample holding portion.

2. A surface plasmon enhanced fluorescence sensor as defined in claim 1, wherein:
    the non flexible film is formed by a polymer.

3. A surface plasmon enhanced fluorescence sensor as defined in claim 2, further comprising:
    hydrophilic linkers that bond with a specific substance and are formed on the non flexible polymer film.

4. A surface plasmon enhanced fluorescence sensor as defined in claim 3, further comprising:
    capture molecules that bond with a specific substance, and are immobilized on the non flexible film.

5. A surface plasmon enhanced fluorescence sensor as defined in claim 2, further comprising:
    capture molecules that bond with a specific substance and are immobilized on the non flexible film.

6. A surface plasmon enhanced fluorescence sensor as defined in claim 1, further comprising:
    capture molecules that bond with a specific substance and are immobilized on the non flexible film.

7. A surface plasmon enhanced fluorescence sensor as defined in claim 6, wherein:
    the capture molecules bond with second messengers within living tissue.

8. A surface plasmon enhanced fluorescence sensor as defined in claim 7, further comprising:
    a kit that causes a labeled substance, which is an integrated substance constituted by the specific substance that directly bonds with the capture molecules and a fluorescent substance excited by the evanescent waves, to be included within the sample.

9. A fluorescence detecting method that employs the surface plasmon enhanced fluorescence sensor defined in claim 7, comprising:
    causing a labeled substance, which is an integrated substance constituted by the specific substance that directly bonds with the capture molecules and a fluorescent substance excited by the evanescent waves, to be included within the sample; and
    detecting the fluorescence.

10. A surface plasmon enhanced fluorescence sensor as defined in claim 6, further comprising:
    a kit that causes a labeled substance, which is an integrated substance constituted by the specific substance that directly bonds with the capture molecules and a fluorescent substance excited by the evanescent waves, to be included within the sample.

11. A fluorescence detecting method that employs the surface plasmon enhanced fluorescence sensor defined in claim 10, comprising:
    causing a labeled substance, which is an integrated substance constituted by the specific substance that directly bonds with the capture molecules and a fluorescent substance excited by the evanescent waves, to be included within the sample; and
    detecting the fluorescence.

12. A fluorescence detecting method that employs the surface plasmon enhanced fluorescence sensor defined in claim 6, comprising:
    causing a labeled substance, which is an integrated substance constituted by the specific substance that directly bonds with the capture molecules and a fluorescent substance excited by the evanescent waves, to be included within the sample; and
    detecting the fluorescence.

* * * * *